United States Patent

Schulten et al.

[11] 4,085,200
[45] Apr. 18, 1978

[54] THERMOCHEMICAL PROCESS FOR PRODUCING METHANE AND OXYGEN

[75] Inventors: Rudolf Schulten, Richterich; Friedrich Behr, Gross Denkte, both of Germany

[73] Assignee: Rheinische Braunkohlenwerke AG., Cologne, Germany

[21] Appl. No.: 768,701

[22] Filed: Feb. 15, 1977

[30] Foreign Application Priority Data

Feb. 20, 1976 Germany ............................ 2606886

[51] Int. Cl.² .................. C01B 13/02; C07C 9/04
[52] U.S. Cl. .................. 423/579; 260/676 R
[58] Field of Search ............... 423/579, 481, 507, 648, 423/679; 260/676 R

[56] References Cited

U.S. PATENT DOCUMENTS

| 3,969,493 | 7/1976 | Fujii et al. ............................ 423/648 |
| 3,984,530 | 10/1976 | Dreyfuss et al. ................. 423/648 X |
| 3,995,016 | 11/1976 | Kittle ................................... 423/579 |

FOREIGN PATENT DOCUMENTS

2,516,441  10/1975  Germany .............................. 423/648

*Primary Examiner*—Edward J. Meros
*Attorney, Agent, or Firm*—Burns, Doane, Swecker & Mathis

[57] ABSTRACT

The invention comprises a recirculatory process for producing methane and oxygen in which iodine and an oxide in a lower valency stage are reacted with methanol, dimethylether or a mixture thereof at an elevated temperature to form the corresponding oxide having a higher valency stage and methyl iodide, the methyl iodide is reacted with water to form hydrogen iodide and reform the methanol and/or dimethylether, the hydrogen iodide is reacted with carbon dioxide to form methane and water and the oxide in the higher valency state is decomposed to release oxygen and reform the oxide having a lower valency stage, the methane and released oxygen are removed and the remaining components are recirculated.

16 Claims, 2 Drawing Figures

THERMOCHEMICAL PROCESS FOR PRODUCING METHANE AND OXYGEN

SPECIFICATION

This invention relates to a multi-stage thermochemical circulatory process for producing methane from carbon dioxide and water.

It is known to decompose water into its components hydrogen and oxygen by using heat and chemical compounds carried in a circuit, the hydrogen obtained subsequently being catalytically reacted with carbon dioxide to form methanol (e.g., see U.S. Pat. No. 1,875,714) and then converting the methanol to methane (e.g., see U.S. Pat. No. 3,928,716). Methane is suitable for the production of energy, since there is no need to modify the distribution network nor the consumers' technical installations. Since carbon dioxide can be extracted from the flue gas of coal-fired power plants and power plants which use natural gas and can be reduced with hydrogen to form methane, a process which utilizes the hydrogen obtained from water undoubtedly constitutes a simple form of recycling carbon.

The manufacturing process used for this purpose should have as its object, inter alia, the following desirable characteristics: firstly, in order to facilitate passage, only liquid or gaseous components should be conveyed in the circuit; secondly, highly corrosive components should only be used at temperatures below approximately 500° C; thirdly, the endothermic reaction, which must take place at very high temperatures in order to obtain high efficiency, should serve to separate oxygen. This renders it possible to form a corrosion-resistant oxide coating in the parts of the plant which transfer heat. Furthermore, a further object should be to minimize the total number of processing steps and to utilize, for the process, the exothermic heat of the reaction of carbon dioxide with hydrogen so that the reduction of carbon dioxide to form methane should not be effected as an additional or subsequent processing step of a water decomposing plant, but should be incorporated as an integral part of a recirculatory process. It is a further object of the invention that pure hydrogen not be produced and reacted separately and subsequently, but that a hydrogen carrier component of the circuit which derives its hydrogen from reaction of a precursor with water be used to react with carbon dioxide to form methane.

These and other objects are achieved according to the present invention by providing a recirculatory process for producing methane and oxygen which comprises:

a. Reacting iodine and an oxide in a lower valency stage with a reactant selected from the group consisting of methanol, dimethylether and a mixture of methanol and dimethylether at an elevated temperature to form the corresponding oxide having a higher valency stage and methyl iodide;

b. Hydrolysing the so formed methyl iodide to form hydrogen iodide and re-form the dimethylether and/or methanol;

c. Reacting the so formed hydrogen iodide with carbon dioxide to form methane and re-form iodine and water;

d. Decomposing the oxide in a higher valence stage into the corresponding oxide in a lower valence stage and releasing oxygen, and in which the oxygen released in (d) and the methane formed in (c) are removed from the system whilst the remaining components are re-utilised in reactions (a) to (d).

In the method of the invention reaction in (a) produces a precursor in methyl iodide in which on reaction with water (b) forms hydrogen iodide which is the hydrogen carrier component which reacts with carbon dioxide to form methane (c).

The oxides having a low valence, i.e. having a low oxygen content, thereby act as oxygen acceptors. Such oxides may be an oxide of sulphur, antimony, vanadium, arsenic, uranium, tellurium, bismuth or selenium. The oxides of vanadium, antimony and arsenic can be used as acceptors in the presence of water. Owing to their higher solubility, the use of oxides of vanadium, antimony, arsenic, uranium, tellurium, bismuth and selenium in the form of alkali salts thereof is preferable to the use of pure or aqueous oxides.

Reaction (a) is preferably conducted at 140° to 240° C, reaction (b) at from 120° to 240° C, reaction (c) at from 25° to 400° C and decomposition (d) at from 850° to 950° C. All the reactions (a) to (d) are preferably conducted at super-atmospheric pressure. Thus reaction (a) is preferably conducted at from 40 to 100 absolute atmospheres reaction (b) at from 20 to 80 absolute atmospheres reaction (c) at from 40 to 80 absolute atmospheres and decomposition (d) at from 20 to 30 absolute atmospheres.

The following processes with aqueous oxides are given by way of example.

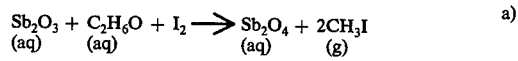
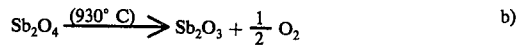
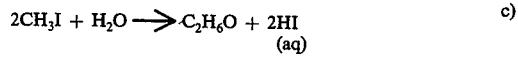
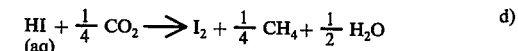
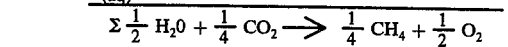

aq = aqueous
g = gaseous

Dimethylether can be replaced by methanol or a mixture of the two compounds. The antimony oxide can be replaced by, for example, vanadium-IV-oxide or arsenic-III-oxide. The oxides $V_6O_{13}$ and $As_2O_5$ formed therefrom can be thermally reconverted to the starting oxides with the giving-off of oxygen.

The following generally recirculatory process can be realised with the corresponding alkali compounds, for example with that of vanadium;

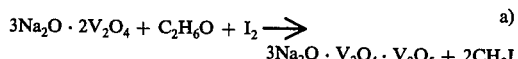
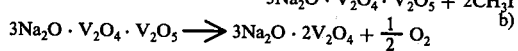
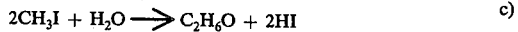
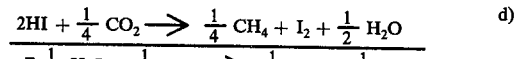
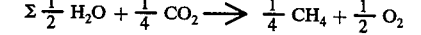

Owing to the relatively simple transportability, it is advantageous to use sulphur dioxide as the oxygen acceptor. By way of example, the recirculatory system can then be as follows:

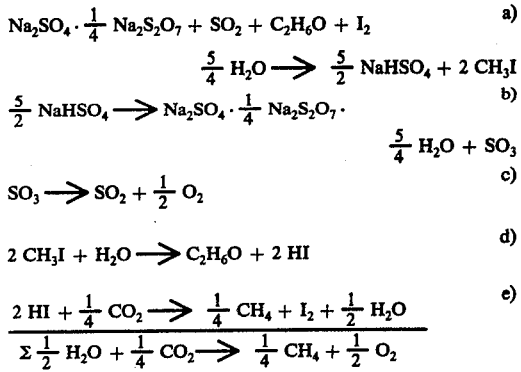

a) $Na_2SO_4 \cdot \frac{1}{4} Na_2S_2O_7 + SO_2 + C_2H_6O + I_2$
$\frac{5}{4} H_2O \rightarrow \frac{5}{2} NaHSO_4 + 2 CH_3I$ b) $\frac{5}{2} NaHSO_4 \rightarrow Na_2SO_4 \cdot \frac{1}{4} Na_2S_2O_7 \cdot$
$\frac{5}{4} H_2O + SO_3$ c) $SO_3 \rightarrow SO_2 + \frac{1}{2} O_2$ d) $2 CH_3I + H_2O \rightarrow C_2H_6O + 2 HI$ e) $2 HI + \frac{1}{4} CO_2 \rightarrow \frac{1}{4} CH_4 + I_2 + \frac{1}{2} H_2O$ $\Sigma \frac{1}{2} H_2O + \frac{1}{4} CO_2 \rightarrow \frac{1}{4} CH_4 + \frac{1}{2} O_2$ The reintroduction of the sulphate-pyrosulphate melt necessary in this instance can be dispensed with if sulphur dioxide is used in a pure or aqueous form, thus resulting in a particularly advantageous process:

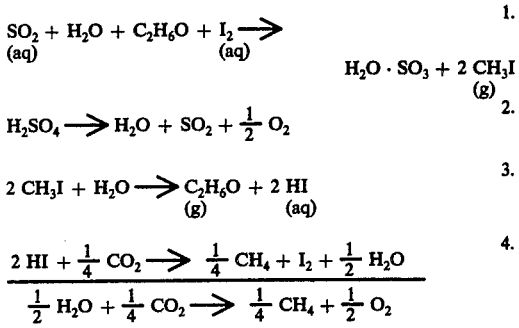

1. $SO_2 + H_2O + C_2H_6O + I_2 \rightarrow$
   (aq)       (aq)
   $H_2O \cdot SO_3 + 2 CH_3I$
   (g)

2. $H_2SO_4 \rightarrow H_2O + SO_2 + \frac{1}{2} O_2$

3. $2 CH_3I + H_2O \rightarrow C_2H_6O + 2 HI$
   (g)         (aq)

4. $2 HI + \frac{1}{4} CO_2 \rightarrow \frac{1}{4} CH_4 + I_2 + \frac{1}{2} H_2O$ $\frac{1}{2} H_2O + \frac{1}{4} CO_2 \rightarrow \frac{1}{4} CH_4 + \frac{1}{2} O_2$ By way of example, an approximately 70 to 75% sulphuric acid concentration can be obtained when the total solution is heated very rapidly, for example from 25° to 240° C, by, for example, dropping it onto a hot shaped substrate made from glass. The rate of vaporization of the methyl iodide is then rendered more rapid than that of the back reaction. Thus, for example, one can work with molar ratios of $CH_3OH/I_2 = 2/1$ to $3/1$, initial concentrations in $H_2SO_4$ of, for example, 60% to 65%, final concentrations of, for example 70% to 75%, a pressure of 1 to 75 absolute atmospheres, starting solutions being chosen which have been saturated with sulphur dioxide at, for example, 20° to 30° C after introducing $CH_3OH$ and iodine.

The solution can also be stripped with sulphur dioxide at, for example 50° C and additionally acidified with hydrochloric acid. The equilibrium is thereby displaced to the right:

$CH_3OH + H^+ + I^- \rightarrow CH_3I + H_2O$

It is possible that sulphur might be formed as a product of an undesirable reversible reaction of sulphur dioxide and water. However, this is prevented with increasing temperature and sulphuric acid concentration with increased total pressures. Temperature, partial pressure of iodine and the dwell time of methanol and-/or dimethyl either have to be correspondingly adjusted. In general, one works at approximately 40 to 100 absolute atmospheres, 140° to 240° C and with 65 to 80% sulphuric acid. The dwell time in, for example, a column type reactor should be less than 1 minute with regard to methanol and/or dimethyl ether.

If all the components are considered to be ideal gases, and if it is assumed that all the other components are substantially less soluble in sulphuric acid than in water at the specified pressures and temperatures, so that the activity of aqueous sulphuric acid is not affected, the following gas composition above sulphuric acid of 80% concentration obtains at, for example 500° K, expressed in absolute atmospheres.

$I_2 = 1.5$; $SO_2 = 10$; $CH_3OH = 1$; $C_2H_6O = 14.54$; $CH_3I = 26.26$; $H_2O = 2.15$; $H_2SO_4 = 5.66 \cdot 10^{-4}$; $HI = 1.39 \cdot 10^{-4}$.

Reaction 1 constitutes as essential step in accordance with the invention since, in this instance, with the use of dimethyl ether/methanol, the decomposition products of water can be separated by means of gaseous/liquid components in accordance with $H_2O + I_2 \rightarrow 2 H^+ + IO^- + I$ with the secondary reaction $HSO^- = IO \rightarrow HSO_4^- + I^-$ The separation of sulphuric acid or sulphur trioxide is known as the reversal of the contact process with, for example, $V_2O_5$ acting as a catalyst. Pressures of 20 to 30 absolute atmospheres and separating temperatures of 850 to 950° C appear to be particularly suitable. The hydrolysis of methyl iodide with small concentrations and at temperatures of approximately 100° C is known per se. Dimethyl ether, dissolved hydrogen iodide and methanol are formed in the presence of methanol in increased concentrations. In order to obtain as highly a concentrated hydrogen iodide solution as possible, it is advantageous to work at temperatures of 160° to 240° C and pressures of 20 to 80 absolute atmospheres. However, it is also particularly advantageous to use dissolved compounds such as $CdI_2$, $ZnI_2$, $HgI_2$ and $CuI_2$ which shift the equilibrium of hydrolysis to the right by sequestering with hydrogen iodide, so that temperatures of 120° to 180° C and pressures of from 10 to 50 absolute atmospheres are adequate. In order to carry out the fourth reaction, one can, for example vaporize a solution of hydrogen iodide and thus obtain hydrogen and iodine in the gas phase, in addition to water vapour and nonreacted hydrogen iodide. It may also be advantageous to heat the hydrogen iodide solution to approximately 250° to 400° C and to subject it to the direct action of carbon dioxide without vaporizing any substantial proportion of the water. The thermal consumption of this reaction can be largely met from the exothermic, superimposed reaction of hydrogen with carbon dioxide. This total reaction constitutes a further essential step in accordance with the invention. Ranges of from 40 to 80 absolute atmospheres and from 25° to 400° C are suitable for carrying out the reaction. It may be advantageous to use conventional hydrogenation catalysts such as platinum, nickel-and copper compounds such as CuI or, alternatively, compounds of the elements of the eighth group. Molecular sieves may also be used.

Figure 1:
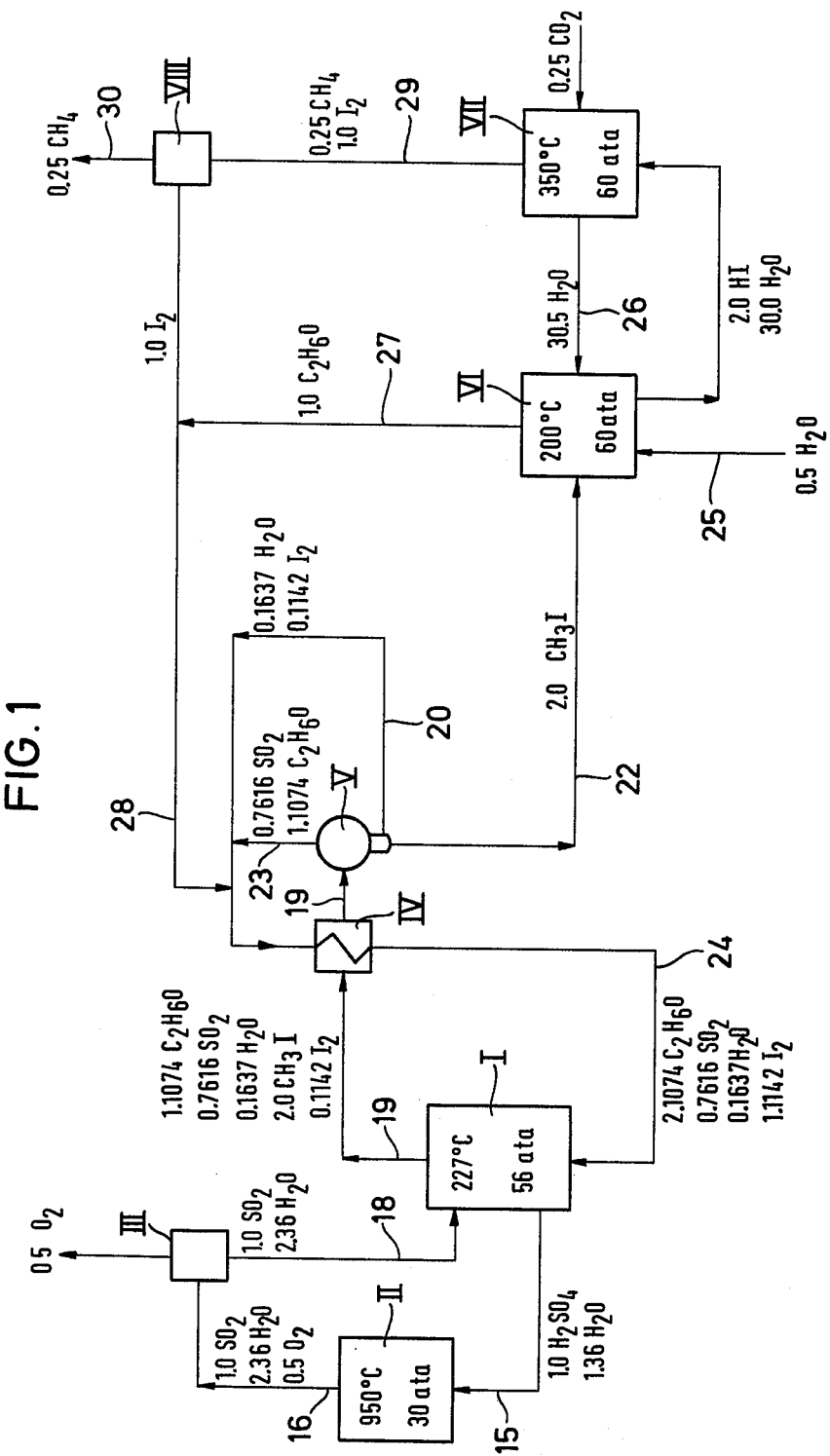
FIG. 1 is a flow-diagram illustrating one embodiment of the invention in which the changeable oxide is $SO_2$.

Referring to FIG. 1, the mass balance is given hereinafter in molar numbers per 0.5 mol of $O_2$.

1.0 of $SO_2$, 2.36 of $H_2O$ are fed to the reactor I by way of the pipe 18, and 2.1074 of $C_2H_6O$, 0.7616 of $SO_2$, 0.1637 of $H_2O$ and 1.1142 of $I_2$ are fed to the reactor I by way of the pipe 24. At a temperature of approximately 227° C and a pressure of approximately 56 absolute atmospheres, 1.0 of $SO_2$ is reacted in the reactor I with 1.0 of $C_2H_6O$ and 2.36 of $H_2O$ and 1.0 of $I_2$ in accordance with equation 1 to form 1.0 of $SO_3$, 2.36 of $H_2O$ and 2.0 of $CH_3I$. 1.0 of $SO_3$ and 2.36 of $H_2O$ are fed to a reactor II by way of a pipe 15. The $SO_3$ is catalytically decomposed in the reactor II at a temperature of approximately 950° C and a pressure of 30 absolute atmospheres, so that 1.0 of $SO_2$, 2.36 of $H_2O$ and 0.05 of $O_2$ leave the reactor II and are fed to an apparatus III by way of a pipe 16. The oxygen (0.5 of $O_2$) is separated out in the apparatus III and is removed from the process by way of a pipe 17. The remaining 1.0 of $SO_2$ and 2.36 of $H_2O$ are returned to the reactor I by way of a pipe 18. 2.0 of $CH_3I$ 1.1074 of $C_2H_6O$, 0.7616 of $SO_2$, 0.1637 of $H_2O$ and 0.1142 of $I_2$ are removed from the reactor I by way of the second outlet pipe 19 and are introduced into a separating apparatus V by way of a heat exchanger IV. The water is condensed in the separating apparatus V and, together with the iodine, is fed as the first liquid phase to a pipe 21 by way of a pipe 20 (0.1637 of $H_2O$, 0.1142 of $I_2$). The only slightly soluble methyl iodide (2.0 of $CH_3I$) is obtained as a second, heavier liquid phase and is conducted into the reactor VI by way of a pipe 22. The other products, namely 0.7616 of $SO_2$ and 1.1074 of $C_2H_6O$ are also fed to the pipe 21 by way of a pipe 23.

The methyl iodide is hydrolyzed in the reactor VI at approximately 200° C and approximately 60 absolute atmospheres. For this purpose, a total of 31.0 of $H_2O$ are introduced into the reactor VI in addition to 2.0 of $CH_3I$, 0.5 of the $H_2O$ being fed from the outside by way of a pipe 25, and 30.5 of the $H_2O$ being fed from a reactor VII by way of a pipe 25. Dimethyl ether (1.0 of $C_2H_6O$) is predominantly produced in the reactor VI in addition to a small quantity of methanol. The dimethyl ether flows through a pipe 27 into a pipe 28 which is connected to the collecting pipe 21 leading to the reactor I. The hydrogen iodide solution (2.0 of HI and 30.0 of $H_2O$) further produced in the reactor VI is catalytically reacted with 0.25 of $CO_2$ in the reactor VII at approximately 350° C and approximately 60 absolute atmospheres. 0.25 of $CH_4$ and 1.0 of $I_2$ are thereby produced and are fed by way of a pipe 29 to a separating apparatus VIII in which the methane is separated from the iodine and from the mixture of $CO_2$ and HI which also exists. The separated methane is removed from the process by way of a pipe 30. The iodine (1.0 of $I_2$) enters the pipe 28 and then, by way of the pipes 21 and 24, together with the other products flowing in these pipes, flows into the reactor I by way of the heat exchanger VI in which the mixture is preheated.

Figure 2:
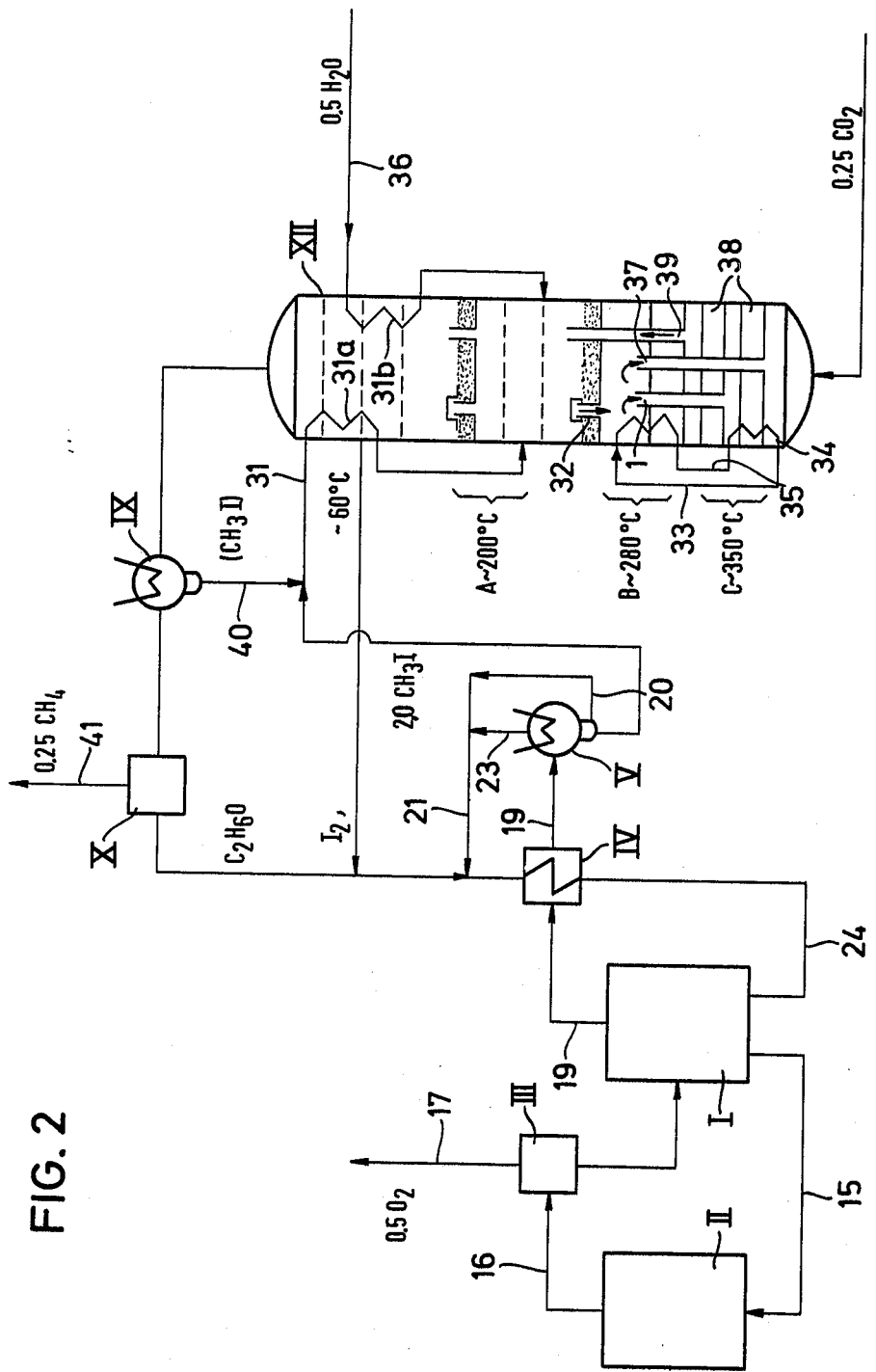
FIG. 2 is a flow-diagram of another embodiment again utilizing $SO_2$ as the changeable oxide.

A variant of the process in accordance with the invention is shown diagrammatically in FIG. 2. The reactors and apparatus I to VI are identical to those of the embodiment of FIG. 1 with respect to their correlation by way of the pipes 15 to 24 and with respect to their functions.

The essential difference resides in the fact that the hydrolysis of the methyl iodide and the catalytic reaction of hydrogen iodide with carbon dioxide are carried out in a single column XII. The hydrolysis is effected in the region A at approximately 200° C. 2.0 of $C_3I$ and 0.5 of $H_2O$ are introduced into this region by way of pipes 31 and 36 respectively. The two pipes 31 and 36 pass through respective heat exchangers 31a and 31b arranged within the column XII. The methyl iodide and the water are preheated in the heat exchangers to a temperature of approximately 60° C. The heat required for this purpose is derived from the partially condensing products rising within the column XII.

The aqueous solution of hydrogen iodide produced in region A flows through pipes 32 into region B in which it is vaporized at a temperature of approximately 280° C. The heat required for this purpose is fed by way of a pipe 33 which is connected to an apparatus 34 by means of which the heat, produced in the region C located therebelow, is carried off. It will be seen from the drawing that a circuit between the regions B and C is closed by means of a pipe 35. The aqueous hydrogen iodide solution vaporized in region B is introduced, under preheating, into the region C by way of gravity pipes 37 and is reacted with carbon dioxide in catalyst beds 38 in the region C. This reaction is effected at a temperature of approximately 350° C. The products produced in region C enter the upper portion of the column XII by way of uptake pipes 39. The upper components are condensed or dissolved by utilizing their heat. The gases dimethyl ether, methane and, if required carbon dioxide as well as non-condensed methyl iodide are separated from one another in the apparatus IX and X. The non-reacted methyl iodide is separated out in IX and is fed into the pipe 31 by way of the pipe 40. The methane is separated out in X and is conducted out of the process by way of a pipe 41.

We claim:

1. A recirculatory process for producing methane and oxygen which comprises:
   a. reacting iodine and an oxide in a lower valency stage with a reactant selected from the group consisting of methanol, dimethylether and a mixture of methanol and dimethylether at an elevated temperature to form the corresponding oxide having a higher valency stage and methyl iodide;
   b. hydrolysing the so formed methyl iodide to form hydrogen iodide and re-form the dimethylether and/or methanol;
   c. reacting the so formed hydrogen iodide with carbon dioxide to form methane and re-form iodine and water;
   d. decomposing the oxide in a higher valence stage into the corresponding oxide in a lower valence stage and releasing oxygen, and in which the oxygen released in (d) and the methane formed in (c) are removed from the system whilst the remaining components are re-utilised in reactions (a) to (d).

2. A method as claimed in claim 1 in which the oxide of lower valency state is selected from the group consisting of the oxides of sulphur, antimony, vanadium, arsenic, uranium, tellurium, bismuth and selenium.

3. A process as claimed in claim 2 in which the oxide having a lower valence stage is a metal oxide and is used in the form of an alkali salt thereof.

4. A method as claimed in claim 1 in which reaction (a) is conducted at a temperature from 140° through 240° C.

5. A method as claimed in claim 1 in which reaction (b) is effected at a temperature from 120° through 240° C.

6. A method as claimed in claim 1 in which reaction (c) is effected at a temperature from 25° through 400° C.

7. A method as claimed in claim 1 in which the decomposition (d) of the oxide having a higher valence stage is effected in the presence of a catalyst.

8. A process as claimed in claim 7 in which the decomposition is effected at a temperature of from 850° through 950° C.

9. A method as claimed in claim 1 in which the reactions (a) to (d) are effected at super-atmospheric pressure.

10. A method as claimed in claim 9 in which reaction (a) is effected at a pressure of from 40 through 100 absolute atmospheres.

11. A method as claimed in claim 9 in which reaction (b) is effected at a pressure of from 20 through 80 absolute atmospheres.

12. A method as claimed in claim 9 in which reaction (c) is effected at a pressure of from 40 through 80 absolute atmospheres.

13. A method as claimed in claim 9 in which the decomposition (d) is effected at a pressure of from 20 through 30 absolute atmospheres.

14. A recirculatory process for producing methane and oxygen which comprises:
 a. reacting iodine and an oxide in a lower valency stage with a reactant selected from the group consisting of methanol, dimethylether and a mixture of methanol and dimethylether at a temperature of from 140° through 240° C and at a pressure of from 40 to 100 absolute atmospheres to form the corresponding oxide having a higher valency stage and methyl iodide;
 b. hydrolysing the so formed methyl iodide at a temperature of from 120° through 240° C and at a pressure of from 20 through 80 absolute atmospheres to form hydrogen iodide and re-form the dimethylether and/or methanol;
 c. reacting the so formed hydrogen iodide with carbon-dioxide at a temperature of from 25° through 400° C and at a pressure of from 40 through 80 absolute atmospheres to form methane and re-form iodine and water;
 d. decomposing the oxide in a higher valence stage in the presence of a catalyst at a temperature of from 850° through 950° C and at a pressure of 20 through 30 absolute atmospheres into the corresponding oxide in a lower valence stage and releasing oxygen, and in which the oxygen released in (d) and the methane formed in (c) are removed from the system whilst the remaining components are re-utilised in reactions (a) to (d).

15. A method as claimed in claim 14 in which the oxide of lower valency state is selected from the group consisting of the oxides of sulphur, antimony, vanadium, arsenic, uranium, tellurium, bismuth and selenium.

16. A method as claimed in claim 14 in which the catalyst in reaction (d) is vanadium pentoxide.

* * * * *